United States Patent [19]

Eaton

[11] Patent Number: 5,073,171
[45] Date of Patent: Dec. 17, 1991

[54] BIOCOMPATIBLE MATERIALS COMPRISING ALBUMIN-BINDING DYES

[76] Inventor: John W. Eaton, Carriage House, 57 Groveland Ter., Minneapolis, Minn. 55403

[21] Appl. No.: 296,496

[22] Filed: Jan. 12, 1989

[51] Int. Cl.$^5$ ............................................. A61M 5/32
[52] U.S. Cl. ........................................ 604/266; 623/1; 623/12; 623/2; 427/2
[58] Field of Search ................ 604/266; 623/1, 2, 12; 427/2

[56] References Cited

U.S. PATENT DOCUMENTS

| | | | |
|---|---|---|---|
| 2,084,399 | 6/1937 | Kuettel | 106/22 |
| 2,874,146 | 2/1959 | Deverell-Smith et al. | 260/45.85 |
| 3,137,671 | 6/1964 | Bosshard et al. | 260/37 |
| 3,325,436 | 6/1967 | Prindle et al. | 260/29.7 |
| 3,453,194 | 7/1969 | Bennett et al. | 204/159.12 |
| 3,585,647 | 6/1971 | Gajewski et al. | 3/1 |
| 3,617,344 | 11/1971 | Leininger et al. | 117/47 |
| 3,625,745 | 12/1971 | Wright et al. | 117/93.31 |
| 3,673,612 | 7/1972 | Merrill et al. | 3/1 |
| 3,677,800 | 7/1972 | Wright | 117/93.31 |
| 3,759,788 | 9/1973 | Gajewski et al. | 195/1.8 |
| 3,826,678 | 7/1974 | Hoffman et al. | 117/81 |
| 3,846,353 | 11/1974 | Grotta | 260/9 |
| 3,888,833 | 6/1975 | Lednicer et al. | 260/79.3 R |
| 3,987,797 | 10/1976 | Stephenson | 128/335.5 |
| 4,152,411 | 5/1979 | Schall | 424/1 |
| 4,273,873 | 6/1981 | Sugitachi et al. | 435/180 |
| 4,378,224 | 3/1983 | Nimni et al. | 8/94.11 |
| 4,526,714 | 7/1985 | Feijen et al. | 260/112 R |
| 4,536,179 | 8/1985 | Anderson et al. | 604/266 |
| 4,600,652 | 7/1986 | Solomon et al. | 428/423.3 |
| 4,676,975 | 6/1987 | McGary et al. | 424/423 |
| 4,795,475 | 1/1989 | Walker | 623/66 |
| 4,879,109 | 11/1989 | Hunter | 424/83 |
| 4,880,788 | 11/1989 | Moake et al. | 514/150 |
| 4,895,566 | 1/1990 | Lee | 604/266 |
| 4,933,178 | 6/1990 | Capelli | 424/78 |
| 4,979,959 | 12/1990 | Guire | 623/66 |

FOREIGN PATENT DOCUMENTS

| | | | |
|---|---|---|---|
| 949 | 3/1979 | European Pat. Off. | 623/1 |
| 290642 | 11/1988 | European Pat. Off. | 623/1 |
| 2143217 | 3/1973 | Fed. Rep. of Germany | 623/1 |
| 2350050 | 4/1974 | Fed. Rep. of Germany | 427/2 |
| 46-37433 | 11/1971 | Japan | 427/2 |
| 39983 | 3/1979 | Japan | 604/266 |
| 0118698 | 9/1979 | Japan | 604/266 |
| 54-135823 | 10/1979 | Japan . | |
| 55-9656 | 1/1980 | Japan . | |
| 57-117560 | 7/1982 | Japan . | |
| 57-117561 | 7/1982 | Japan . | |
| 57-119950 | 7/1982 | Japan . | |
| 136351 | 8/1983 | Japan | 604/266 |
| 0179255 | 7/1988 | Japan . | |
| 0261164 | 10/1988 | Japan . | |

OTHER PUBLICATIONS

*The Merck Index*, S. Budavare, Ed., Merck & Co. (11th ed. 1989) at p. 5979.
T. H. Maugh, II, *Science*, 217, 1129–1130 (1982).
H. E. Kambic et al., *Chem. Eng. News*, 30–48 (Apr. 14, 1986).
P. D. G. Dean et al., *J. Chromatography*, 165, 301–319 (1979).
B. Arkles, "Silane Coupling Agent Chemistry", pp. 54–55, Petrarch Systems, Bristol, PA.
W. J. Williams et al., *Hematology*, p. 1641 (2nd ed., 1977).
H. R. Baumgartner, *Microvasc. Res.*, 5, 167–179 (1973).

Primary Examiner—C. Fred Rosenbaum
Assistant Examiner—Mark O. Polutta
Attorney, Agent, or Firm—Merchant, Gould, Smith, Edell, Welter & Schmidt

[57] ABSTRACT

A biocompatible prosthetic device is provided which comprises a solid polymeric body incorporating an amount of an albumin-binding dye effective to form a coating of endogenous albumin on said device when the device is in contact with a physiological fluid containing albumin. A method of increasing the albumin-binding ability of a prosthetic device is also provided.

22 Claims, 3 Drawing Sheets

BIOCOMPATIBLE MATERIALS COMPRISING ALBUMIN-BINDING DYES

FIELD OF THE INVENTION

The present invention relates generally to polymeric materials having increased ability to bind albumin from a physiological fluid containing albumin, and more particularly to biomaterials used as components of medical devices comprising said polymeric materials.

BACKGROUND OF THE INVENTION

A. Iatrogenic Effects of Implantable Devices

Implantable medical devices made of various materials may cause a number of iatrogenic effects in patients. First, catheters, artificial heart valves, artificial joints, shunts, implanted leads for electrical stimulation devices, and vascular grafts can serve as foci for infection of the body. Infection is promoted by the tendency of bacterial organisms to adhere to the surfaces of implantable devices and, while adherent, to resist destruction by phagocytic cells that normally would destroy these organisms.

Second, catheters, vascular grafts and other implantable devices also tend to serve as a nidus, or focus, for the formation of thrombi (blood clots). This is because the surfaces of the implanted materials may activate non-cellular plasma clotting factors. Furthermore, platelets which adhere to the surfaces of these materials become activated and form thrombi. The procoagulant activities of many materials can prevent their use in vivo, or can greatly diminish their useful lifetime, as in the case of vascular access devices such as catheters. Finally, even materials which are chemically inert may act as foci for the formation of inflammatory lesions such as granulomas, resulting, in many cases, in the necessity for removal of the implanted device.

Therefore, there is a need for methods to render the surfaces of implantable materials less thrombogenic, less pro-inflammatory and less receptive to potentially infective bacteria.

B. Modification of Thrombogenic Materials

The development of implantable medical devices such as artificial organs has been hampered by the lack of suitable synthetic materials which are biologically and chemically stable when contacted with physiological fluids, particularly blood. For example, many conventional plastics and resins, including even highly inert materials such as silicones, are not suitable for long term contact with blood because they are too thrombogenic. See Wright et al., U.S. Pat. No. 3,625,745. However, anticoagulants can be bound to the surface of biologically inert materials to impart antithrombogenic characteristics to the materials. For example, a coating of the anticoagulant heparin on silicone rubber improves the antithrombogenic characteristics of the rubber. See Gajewski et al., U.S. Pat. No. 3,585,647.

Quaternary amines have been bound to polymer surfaces, followed by the binding of heparin thereto. See Leininger et al., U.S. Pat. No. 3,617,344. In contrast, H. M. Grotta disclosed a method in U.S. Pat. No. 3,846,353 in which heparin is complexed with a quaternary amine prior to coating the complex onto the polymer surface. Both the Leininger et al. and Grotta methods have the disadvantage of being non-permanent or leachable systems; i.e. the heparin would gradually be lost from the polymer material into the surrounding medium. In general, ionically bound systems have limited viability due to the instability of the anticoagulant. See Solomon et al., U.S. Pat. No. 4,600,652.

Therefore, there is a need for implantable materials in which the biologically active ingredient (such as an anticoagulant or an agent which might suppress inflammatory response or bacterial adherence) retains its activity in an essentially permanent and non-leachable fashion when the material is exposed to a physiological fluid for extended periods.

C. Albumin Selectivity

Albumin is the predominant plasma protein, readily soluble in water and in constant contact with the luminal surface of the vascular endothelium. The vascular endothelium itself imparts several desirable characteristics to the walls of blood vessels, including diminished tendency to promote coagulation, reduced attractiveness for inflammatory, phagocytic cells, and increased ability to resist colonization by pathogenic bacteria.

In its normal configuration, albumin does not promote clotting nor attract inflammatory cells. It would be desirable to coat the surfaces of medical devices with albumin, thereby imparting these same characteristics to the surfaces of biomaterials. Therefore, there is a need for procedures to selectively adsorb albumin to the surface of implantable devices in order to yield implantable materials with these desirable characteristics.

Coating surfaces with albumin apparently reduces their thrombogenicity, although the reasons for this effect remain unknown. See T. H. Maugh II, *Science*, 217, 1129 (1982). Workers have investigated numerous ways to attract albumin to polymer surfaces. For example, D. J. Lyman of the University of Utah has sought to synthesize new or altered polymers that have an intrinsic attraction for albumin. Lyman has worked primarily with block copolymers of polyethers and polyurethanes. See T. H. Maugh, supra. Additionally, R. E. Eberhart and M. Munro of the University of Texas have found that alkylating polyurethane with $C_{16}-C_{18}$ hydrocarbons results in polymers with very high selectivity for albumin in blood. See T. H. Maugh, supra.

In contrast with methods for increasing the in vivo intrinsic attraction of implantable materials for albumin, other researchers have studied methods of binding albumin directly to the surfaces of medical materials prior to implanting them in the body. For example, Hoffman and Schmer (U.S. Pat. No. 3,826,678) disclose the chemical bonding of biologically active molecules including albumin to hydrophilic hydrogels previously radiation-grafted to inert polymeric substrates such as polyurethane and silicone Feijen et al. (U.S. Pat. No. 4,526,714) disclose a process for the preparation of a conjugate of a water-soluble protein such as albumin with an anticoagulant such as heparin. The conjugate, which comprises a coupling agent such as 1-ethyl-3-dimethylaminopropyl carbodiimide (EDC), forms amide linkages between the heparin and protein. The conjugate is disclosed as suitable for coating surfaces of medical materials.

A disadvantage of prior attempts to attract and/or to bind albumin to polymeric surfaces has been the tendency of components of the substrate material to denature or disrupt the noncovalent structure of the albumin. Such conformational changes can cause a loss of biological activity of the protein. Protein denaturation can also be induced by the changes in temperature and pH which are encountered in albumin-binding reactions. Furthermore, like the soluble albumin which circulates in the plasma, albumin irreversibly bound to a surface is susceptible to ultimate destruction, thereby negating any advantageous effects the bound albumin might have imparted to the surface.

Therefore, there is a need for implantable medical materials which selectively bind albumin, which do not denature the bound albumin, and which foster the spontaneous replacement of any previously bound albumin which has been lost or destroyed.

SUMMARY OF THE INVENTION

The present invention provides biocompatible prosthetic devices comprising polymeric materials which incorporate certain dyes as disclosed herein that have a high and selective affinity for albumin when exposed to a fluid containing albumin, such as a physiolgical fluid. Accordingly, the present invention provides a biocompatible prosthetic device comprising a solid polymeric body incorporating an amount of an albumin-binding dye effective to form a coating of endogenous albumin on the device when the device is in contact with a physiological fluid containing albumin. The albumin-binding dye preferably comprises an aromatic albumin-binding dye which comprises a diazo dye, a sulfonic acid dye, or the physiologically-acceptable salts thereof. In a preferred embodiment of the invention, the albumin-binding dye is present in a conjugate also comprising a physiologically-acceptable, high molecular weight, water-soluble polysaccharide such as dextran.

In another preferred embodiment of the invention, a polymeric body is provided which comprises the dye/polymer conjugate in an amount effective to bind albumin to the surface of the polymeric body. In addition to serving as a coating for, or being cast into, a biocompatible prosthetic device, the polymeric body may be formed into a thin film, a tube, or the like.

The present invention further provides a method of increasing the albumin-binding ability of a prosthetic device.

Advantageously, unlike normal foreign surfaces, the "derivatized" materials of the present invention apparently do not denature the albumin protein upon its adsorption to the materials. Additionally, prosthetic devices made of the present materials are markedly less thrombogenic and attract fewer platelets than devices made of commonly used medical materials. Furthermore, the surfaces of the present devices accumulate fewer adherent bacteria than devices which do not incorporate the dyes or dye/polymer conjugates disclosed herein.

As used herein, the term "endogenous albumin" refers to the albumin which is normally present in a physiological fluid, such as the human serum albumin present in human blood. However, the present "derivatized" materials can also be used to bind albumin from synthetic solutions, thereby precoating the polymeric body with albumin prior to its introduction into a body cavity or contacting it with a physiological fluid ex vivo.

DETAILED DESCRIPTION OF THE INVENTION

A. Biocompatible Implantable Prosthetic Device

Figure 1:
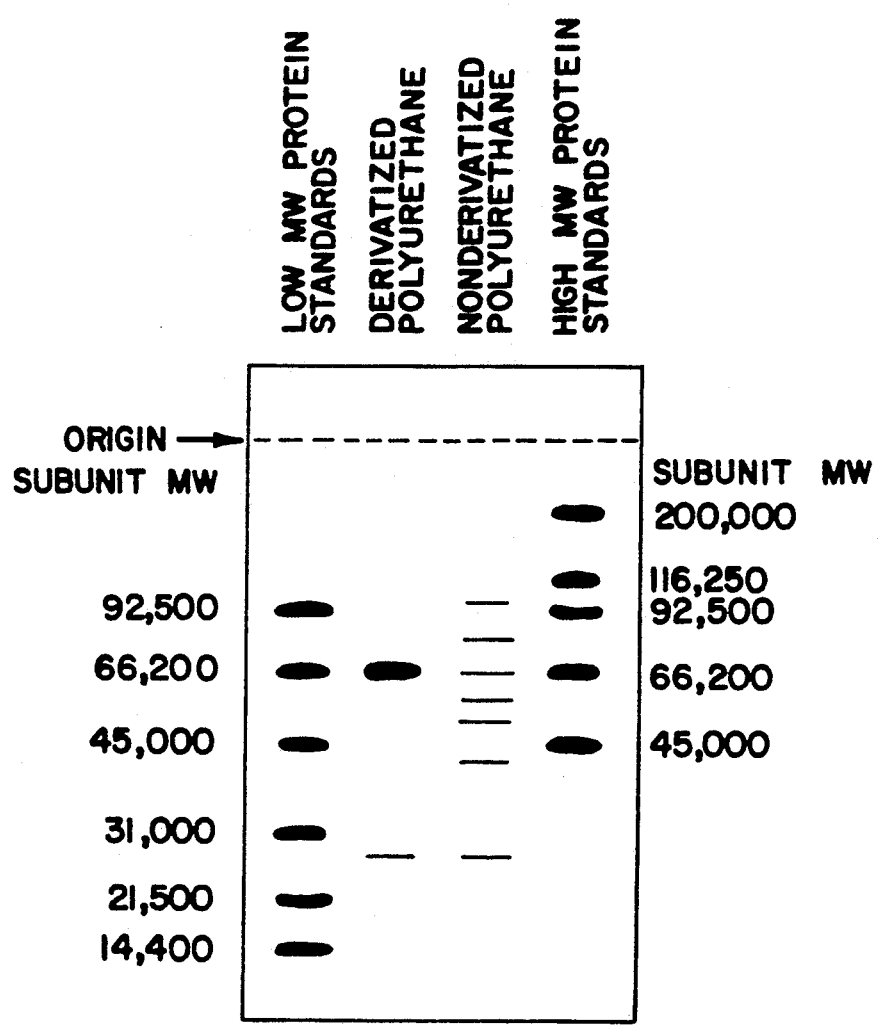
FIG. 1 depicts an SDS-polyacrylamide gel electrophoretogram showing proteins eluted from polyurethane derivatized according to the present method and from non-derivatized polyurethane.

The present invention provides a biocompatible implantable prosthetic device which is implantable or which may contact physiological fluids ex vivo. As used herein, the word "biocompatible" means that the device is compatible with living tissue or systems by being non-toxic, non-thrombogenic, and non-provoking of inflammation. A "prosthetic device" is intended to mean any artificial part or device which replaces or augments a part of a living body. Examples of prosthetic devices which the present invention is intended to encompass include artificial hearts, implantable drug infusion pumps, artificial kidneys, heart valves, vascular grafts, blood oxygenators, catheters, soft or hard tissue substitutes, coatings for sutures, and the like. For a general discussion of implantable devices and biomaterials from which they can be formed, see H. E. Kambic et al., "Biomaterials in Artificial Organs", *Chemical and Engineering News*, 30–48 (Apr. 14, 1986), the disclosure of which is incorporated herein by reference.

The present invention also encompasses polymeric bodies which are contacted with physiological fluids external to the body (ex vivo). These bodies may be used in medical devices for hemodialysis, treatment of hepatic failure, plasmapheresis, blood access, and the like. Examples of such polymeric bodies include thin films, tubes, hollow fibers, beds of beads or other shaped particles (packed or fluidized), microcapsules (coated or encapsulated), and the like.

B. Polymeric Material

The biocompatible prosthetic device of the present invention comprises a solid, shaped, polymeric body. The polymeric material from which the body may be formed includes any high molecular weight, physiologically compatible (i.e., free from toxic catalysts, stabilizers, processing aids, or the like), polymer. Among the polymeric materials especially useful in the present invention are polyurethanes; silicone elastomers; and polycarbonates. Other polymeric materials which may be useful in the present invention include polypropylenes, polyethylenes, polyvinyl chlorides, polyesters, nylons, cellulosics, polyvinyl pyrrolidones, polymethacrylates and polyvinyl alcohols.

Among the polyurethanes suitable for use in the present invention are the elastomeric, segmented polyether polyurethanes derived from repeating units of polytetramethylene ether glycol and a mixture of methylene diisocyanate and a diol (or diamine) coupler. One such material is commercially available under the designation Pellethane TM, from Upjohn, Inc., Torrence, CA. Other suitable commercially available polyether-based polyurethanes include Biomer TM from Ethicon, Inc., Somerville, N.J.; Estane TM (B. F. Goodrich Co., Cleveland, OH.); Tygothane TM (Norton Chemical Co., Akron, OH.); Superthane TM (Newage Industries, Willow Grove, PA.); Renathane TM (Renal Systems, Inc., Minneapolis, MN.); Minor Rubber Co. Polyurethane TM (Mionor Rubber Co., Bloomfield, N.J.); Tecoflex TM (Thermedic, Inc., Woburn, MA.); and SRI 3-2000-1-E TM (SRI, Menlo Park, CA.).

Among the silicone elastomers useful in the present invention are the medical grade elastomers commercially available under the designation Silastic TM from Dow Corning Corp., Midland, MI., in Clean Grades Soft, Medium, and Firm. Another medical grade elastomer is available in paste form under the designation Medical Adhesive, silicone Type A from Dow Corning Corp.

Among the polycarbonates useful in the present invention are included the bisphenol A polycarbonates. One such polycarbonate is sold commercially under the designation Lexan TM by General Electric, Pittsfield, MA. A commercially available silicone rubber/polycarbonate copolymer suitable for use in the present invention is MEM 213, available from General Electric, Pittsfield, Mass.

It should be pointed out that the present method of modifying materials with albumin-binding dyes is not limited to modification of polymeric materials; similar modification procedures can be carried out on a number of implantable materials, including ceramics, metals, cellulosics, natural and synthetic fibers, and the like.

C. Aromatic Albumin-Binding Dyes

The solid polymeric body of the present invention comprises an albumin-binding dye. Preferably the albumin-binding dye comprises an aromatic albumin-binding dye. The aromatic albumin-binding dye preferably comprises a diazo dye; a physiologically-acceptable alkali metal salt, alkaline earth metal salt, or amine salt of said diazo dye; a sulfonic acid dye; a physiologically-acceptable alkali metal salt, alkaline earth metal salt, or amine salt of said sulfonic acid dye; or mixtures thereof.

Aromatic albumin-binding dyes particularly useful in the present invention include Reactive Blue 2 (1-Amino-4[[4-[[4-chloro-6-[[3(or 4)-sulfophenyl]amino]-1,3,5-triazin-2-yl]amino]-3-sulfophenyl]amino]-9,10-dihydro-9,10-dioxo-2-anthracenesulfonic acid), available from Sigma Chemical Company, St. Louis, MI.; Evans Blue (6,6'-(3,3'-Dimethyl [1,1'-biphenyl]-4,4'diyl)bis(azo)]bis[4-amino-5-hydroxy-1,3-naphthalene disulfonic acid] tetrasodium salt), (Sigma); Trypan Blue (3,3'-[3,3'-Dimethyl[1,1'-biphenyl]-4,4'diyl)bis-(azo)]bis[5-amino-4 hydroxy-2,7-naphthalene disulfonic acid] tetrasodium salt), (Sigma); Bromcresol Green (4,4'-(3H-2,1-Benzoxathiol-3-ylidene)bis[2,6-dibromo-3-methylphenol] S,S-dioxide), (Sigma); Bromcresol Purple (4,4'-(3H-2,1-benzoxathiol-3-ylidene)bis[2-bromo-6-methylphenol] S,S-dioxide), (Sigma); Methyl Orange (4-[[(4-dimethylamino) phenyl]azo]benzenesulfonic acid sodium salt), (Sigma); 2-(4'-hydroxyazobenzene)-benzoic acid, (Sigma); Procion red HE 3B, as disclosed by Dean and Watson, J. Chromatoqraphy, 165:301–319 (1979), incorporated herein by reference; and mixtures thereof.

The albumin-binding dye is preferably integrally contained within and throughout the polymeric body as well as on its surface. Alternatively, the dye may be chemically bound to the surface of the solid polymeric body, thereby modifying only the surface of the implant.

D. Dye/Polymer Conjugate

A preferred embodiment of the derivatization of polymers with albumin-binding dyes determines the way in which the albumin associates with the dye. In order to bind, but not to substantially denature the albumin, it is preferable to situate or space the dye some distance from the surface of the polymeric material. Therefore, a preferred embodiment of the present invention includes a polymeric body comprising a conjugate comprising a physiologically acceptable high molecular weight, water-soluble polymer such as a polysaccharide or a polypeptide comprising at least one albumin-binding dye, as defined above. A water-soluble polysaccharide is utilized in order to maximize the extent of surface exposure of the molecules of the albumin-binding dye and their ability to subsequently interact with albumin.

A commercially available polysaccharide suitable for use in the present invention is dextran, available from Sigma Chemical Company, St. Louis, MI. A dextran may be generally defined as a polysaccharide containing a backbone of D-glucose units linked predominantly $\alpha$-D(1->6). Dextran with an average molecular weight of 40,000, designated as "Dextran 40", is commercially available as Gentran 40 TM from Baxter Travenol Laboratories, Deerfield, IL.; as LMD TM from Abbott Laboratories, North Chicago, IL.; and as Rheomacrodex from Pharmacia Fine Chemicals, Uppsala, Sweden. Dextran with an average molecular weight of 75,000, designated "Dextran 75", is commercially available as Gentran 75 TM from Baxter Travenol Laboratories, Deerfield, IL.; and as Macrodex from Pharmacia Fine Chemicals, Uppsala, Sweden.

A commercially-available, pre-mixed form of the conjugate of the present invention is marketed under the designation Blue Dextran by Pharmacia Fine Chemicals, Uppsala, Sweden, and is also commercially available under the same tradename from Sigma Chemical Company, St. Louis, MI. Blue Dextran is prepared from dextran with an average molcular weight of about $2 \times 10^6$ and incorporates approximately 0.1 mmol of the dye Reactive Blue 2 per gram of dextran.

Other biocompatible, water-soluble polysaccharides which can be conjugated to albumin-binding dyes are also useful in the present invention. These include alginates, modified celluloses, modified starches, and the like.

In a preferred embodiment of the present invention, the dye/polymer conjugate is incorporated into the bulk polymeric material, as defined above, thereby presenting a high concentration of the desired dye at the surface of the bulk polymeric material. A substantial number of the total dye molecules are exposed to the extent that they can bind albumin without substantial denaturation of the bound protein. The dye/polymer conjugate can be dissolved in a solution of the bulk polymer or prepolymer in an appropriate solvent. Solvents useful in the present invention include N,N-dimethylacetamide (DMAC) and dimethyl formamide.

The precise ratios of dye/polymer conjugate to solvent to bulk polymer which are used depend on a number of considerations, including the solubility characteristics of the dye preparation and the bulk polymer of choice. Preferably, the derivatized polymeric material of the present invention will be prepared from a dye/polymer conjugate, a bulk polymer, and a solvent, present respectively in an initial weight ratio of about 1:0.5–2:20, more preferably about 1:0.25–4:40, and most preferably about 1:0.25–6:60.

An advantage of this preferred embodiment of the present invention is that the derivatization of the finished material is durable and pervasive. Thus, materials prepared as described herein will retain modified surface characteristics for prolonged periods during in vivo or ex vivo implantation. Furthermore, because the dye permeates the entire material (rather than just being present on the surface), erosion of the original surface will not destroy the unique albumin-binding properties of these materials.

Alternatively, the dye/polymer conjugate may be chemically or ionically bound to the surface of the solid polymeric body, thereby modifying only the surface of the implant. This can be accomplished by dipping, spraying or brushing a solution of the conjugate onto the surface of the polymer and removing the solvent under suitable conditions. Additionally, the albumin-binding dye or its conjugates may be chemically reacted with monomers or polymers of implant materials to produce a final product in which the dye is an integral part of the finished polymer. Such a derivatization procedure may involve the use of chemical couplers. For example, in the case of silicone polymers, the use of organosilane couplers has been described by Arkles, "Silane Coupling Agent Chemistry", pages 54–55, Petrarch Systems, Bristol, PA., the disclosure of which is incorporated herein by reference.

E. Physiological Fluids

The present invention promotes the binding of albumin to a biocompatible prosthetic device when the device is in contact with a physiological fluid containing albumin. Such contact may occur in vitro (ex vivo) or in vivo. Examples of the physiological fluids with which the prosthetic device of the present invention may come into contact include blood, lymph, saliva, urine, tears, and cerebro-spinal fluid.

The invention will be further described by reference to the following detailed examples.

EXAMPLE I

Preparation of Blue Dextran-Derivatized Polyurethane

A. Preparation of Derivatized Polyurethane Film

A derivatized polyurethane was prepared by dissolving 0.32 g of Blue Dextran (Pharmacia Fine Chemicals, Uppsala, Sweden) in 1.5 ml of pure water. This mixture was then added to 20 g of N,N-dimethylacetamide (DMAC) (Fisher Scientific Company, Pittsburg, PA.). To this Blue Dextran/solvent mixture, 1.0 g of Pellethane TM 2363-55D polyurethane (Dow Chemical Company, Midland, MI.) was added. The mixture was shaken overnight to allow solvation of the polyurethane. The solvated Blue Dextran/polyurethane mixture was then cast on a Mylar release sheet and dried overnight at 50° C. to remove the solvent. The weight of the resultant polyurethane/Blue Dextran compound was found to total at least 96% that of the non-solvent components initially added. The resulting derivatized polyurethane film was then tested as described below for protein adsorption, selectivity for albumin, thrombogenicity, interactions with platelets in whole, flowing blood, and adherence of pathogenic bacteria.

B. Assessment of Extent and Durability of the Derivatization of Polyurethane with Blue Dextran Additional experiments were performed to determine the durability and stability of the Blue Dextran conjugate within the polymer. Samples of the derivatized sheeting prepared as in Part A above were incubated in greater than 200 volumes of water or 0.15M NaCl for 90 days at 37° C. The concentration of Blue Dextran which leached out during this period was determined on a mass loss basis. Based upon measurement of sample weights before and after incubation, it was determined that less than 1% of the Blue Dextran incorporated into the polyurethane had been leached into either test solution. Direct spectrophotometric analysis of the aqueous medium by measurement of optical absorption at 616 nm confirmed that less than 1% of the Blue Dextran had been lost. Thus, both types of analysis indicated that the Blue Dextran was strongly incorporated into the polyurethane.

C. The Extent of Surface Adsorption of Whole Human Plasma Proteins on Derivatized Polyurethane Sample discs were cut out of the derivatized polyurethane film prepared as in Part A above and out of non-derivatized polyurethane film. The surface area of each disk was 1.57 cm$^2$. The derivatized and non-derivatized control discs were soaked in whole human plasma at 25° C. for 3 mins. The plasma had previously been collected in acid citrate dextrose (ACD) anticoagulant, heated to 56° C. for 30 mins to inactivate complement, and stored at −20° C. The discs were then washed in three changes of isotonic NaCl solution, with more than 10,000 volumes of solution used in each wash, for a total wash time of 15 mins.

After washing, the discs were removed and placed in 12×75 mm glass culture tubes (Fisher Scientific Company, Pittsburgh, PA.), each containing 1 ml of BCA protein assay reagent (Pierce Chemical Company, Rockford, IL.). Tubes with discs and assay reagent were incubated for 30 mins at 60° C. The reagent was then removed and spectrophotometrically read on a Beckman DU-8 spectrophotometer at a wavelength of 562 nm. The results of the spectrophotometric analysis are shown in Table 1, below.

TABLE 1

Amounts of Whole Human Plasma Protein Adherent to Derivatized and Non-derivatized Polyurethane Samples Following 3 Minutes Incubation at 25° C.
μg Proteins Adsorbed/cm$^2$ of Polyurethane Surface

| Derivatized Polyurethane | Non-derivatized Polyurethane |
|---|---|
| 4.78 | — |
| 5.73 | 5.16 |
| 3.82 | 6.62 |
| 5.10 | 5.16 |
| 3.89 | 7.64 |
| 3.63 | 6.18 |
| avg. = 4.49 ± 0.84 | avg. = 6.15 ± 1.05 |

D. The Extent of Surface Adsorption of Purified Albumin on Derivatized Polyurethane Sample discs each having a surface area of 1.57 cm$^2$ were cut out of derivatized and non-derivatized polyurethane films prepared as in Part A above. The discs were soaked in human serum albumin (25 g/100 ml) at 25° C. for 3 mins., then washed in three changes of isotonic NaCl solution, with more than 10,000 volumes used in each wash, for a total wash time of 15 mins.

After washing, the discs were removed and placed in 12×75 mm glass culture tubes (Fisher Scientific Company, Pittsburgh, PA.) which contained 1 ml of BCA protein assay reagent (Pierce Chemical Company, Rockford, IL.). Tubes with discs and assay reagent were incubated for 30 mins at 60° C. Reagent was then removed and spectrophotometrically analyzed on a Beckman DU-8 spectrophotometer at a wavelength of 562 nm. The results of this experiment are shown in Table 2, below.

TABLE 2

Amounts of Serum Albumin Adherent to Derivatized and Non-derivatized Polyurethane Samples Following 3 Minutes Incubation at 25° C.

$\mu g$ Albumin Adsorbed/$cm^2$ of Polyurethane Surface

| Derivatized Polyurethane | Non-derivatized Polyurethane |
|---|---|
| 5.16 | 1.78 |
| 5.23 | 1.53 |
| avg. = 5.20 | avg. = 1.66 |

E. SDS Gel Electrophoresis of Eluted Surface-Adsorbed Proteins on Derivatized Polyurethane Sample discs each having a surface area of 1.57 $cm^2$ were cut out of derivatized and non-derivatized polyurethane films prepared as in Part A above. The discs were soaked in whole human plasma at 25° C. for 3 mins., then washed as in Part D, above.

After washing, two discs were placed in 12×75 mm glass culture tubes with 100 lambda of Sodium dodecyl sulphate-polyacrylamide gel electrophoresis (SDS-PAGE) sample buffer solution. The buffer solution consisted of 62.5 mM Tris-HCl; 5% 2-mercaptoethanol (Sigma Chemical Company, St. Louis, MI.); 10% glycerol (Sigma); and 2.3% sodium dodecyl sulphate (SDS) (Sigma) in water. SDS-polyacrylamide gel electrophoresis (SDS-PAGE) was then performed on 50 lambda of buffer solution containing the eluted proteins. Following electrophoresis, the gel was stained with Coomassie Brilliant Blue G ™ (Sigma), and the identity of the eluted proteins determined by reference to molecular weight standards included on the gel.

As shown in FIG. 1, the results of these experiments indicate that the major protein adsorbed to the Blue Dextran-derivatized polyurethane is albumin. By contrast, non-derivatized polyurethane had much less adsorbed albumin and proportionately more non-albumin proteins.

F. Clotting Times of Whole Blood in Contact with Derivatized Polyurethane

Whole blood clotting times were studied using glass culture tubes coated with derivatized polyurethane prepared as in Part A above and with non-derivatized polyurethane. The tubes were coated with the polyurethanes by dip coating, with draining of unadsorbed plastic and drying at 50° C. for 24 hours. The rate at which 1 ml of fresh whole blood clotted in these tubes was measured by determining the time required for detectable clot formation to occur after the whole blood was added to the coated tube, as described by Williams et al., Hematology, 1641 (2nd ed., 1977), the disclosure of which is incorporated herein by reference.

Figure 2:
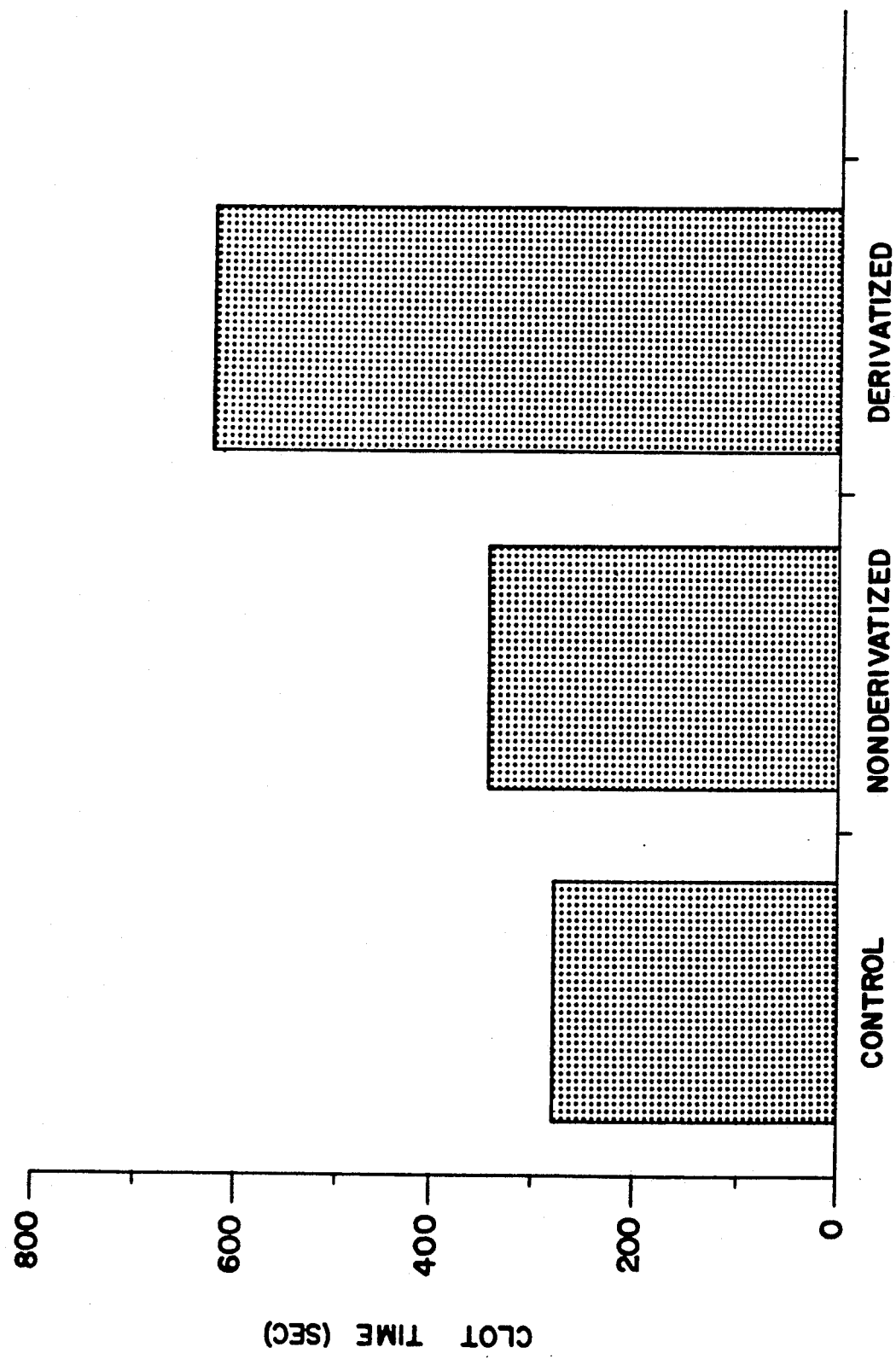
FIG. 2 depicts the clotting time of whole blood in "control" glass tubes, in tubes coated with polyurethane derivatized according to the present method, and in tubes coated with non-derivatized polyurethane.

FIG. 2 depicts the clotting time in seconds of the three types of material tested: control (glass tubes), non-derivatized polyurethane, and derivatized polyurethane. The results depicted in FIG. 2 indicate that polyurethane derivatized with Blue Dextran conjugate resists clotting for a significantly greater length of time than non-derivatized polyurethane.

G. Interactions with Formed Blood Elements

Catheters were prepared from the derivatized polyurethane prepared according to Part A above and from non-derivatized polyurethane. The catheters were inserted in a Baumgartner apparatus constructed according to H. R. Baumgartner, "The Role of Blood Flow in Platelet Adhesion, Fibrin Deposition, and Formation of Mural Thrombi," *Microvasc. Res.*, 5, 167–179 (1973), the disclosure of which is incorporated herein by reference. In the Baumgartner apparatus, whole citrate-anticoagulated blood, maintained at 37° C., is pumped through a chamber containing the material to be tested. In this experiment, blood flow was maintained at a rate of 140 ml/min and a shear rate of 800 $sec^{-1}$. The temperature of the blood was maintained at 37° C. The catheters of derivatized and non-derivatized polyurethane were placed within the chamber of the Baumgartner apparatus and, after exposure to blood flow at the conditions described above for five mins, removed, fixed and stained.

As shown in Table 3 below, the results of this experiment indicate that large numbers of platelets adhered to the non-derivatized polyurethane, whereas almost no detectable platelets adhered to the Blue Dextran-derivatized polyurethane. It was further observed that the large numbers of platelets which were adherent to the control (non-derivatized) material were activated, as indicated by spreading of pseudopodia from the cells; those few platelets found on the derivatized polyurethane were, at least by morphologic criteria, not activated.

TABLE 3

Adherence of Human Platelets to Control and Blue Dextran-Derivatized Polyurethane Under Conditions of Flow in a Baumgartner Device

| Material | Sample No. | Adherent Platelets per $mm^2$ |
|---|---|---|
| Control | 1 | 17,900 |
|  | 2 | 18,900 |
|  | 3 | 26,500 |
|  | 4 | 28,600 |
|  |  | avg. 23,000 |
| Derivatized | 1 | 162 |
|  | 2 | 108 |
|  | 3 | 54 |
|  | 4 | 0 |
|  |  | avg. 81* |

*p < 0.0001 (Student's "t" test, two-tailed).

H. Interactions With Blood Elements In Vivo

Catheters prepared from control (non-derivatized) and from derivatized polyurethane according to Part A above were implanted in a mongrel dog in order to investigate the accumulation of plasma proteins after 24 hours. Both catheters were surgically implanted as bilateral femoral bypasses in the anesthetized dog. Twenty-four hours after surgery, the animal was sacrificed, the catheters removed, and the loosely adherent proteins removed by washing with saline. The polyurethane catheters were than treated with 62.5 mM Tris- HCl; 5% 2-mercaptoethanol (Sigma Chemcal Company, St. Louis, MI.); 10% glycerol (Sigma); and 2.3% sodium dodecyl sulphate (SDS) (Sigma) in water. The eluate was subjected to standard SDS-polyacrylamide gel electrophoresis.

Figure 3:
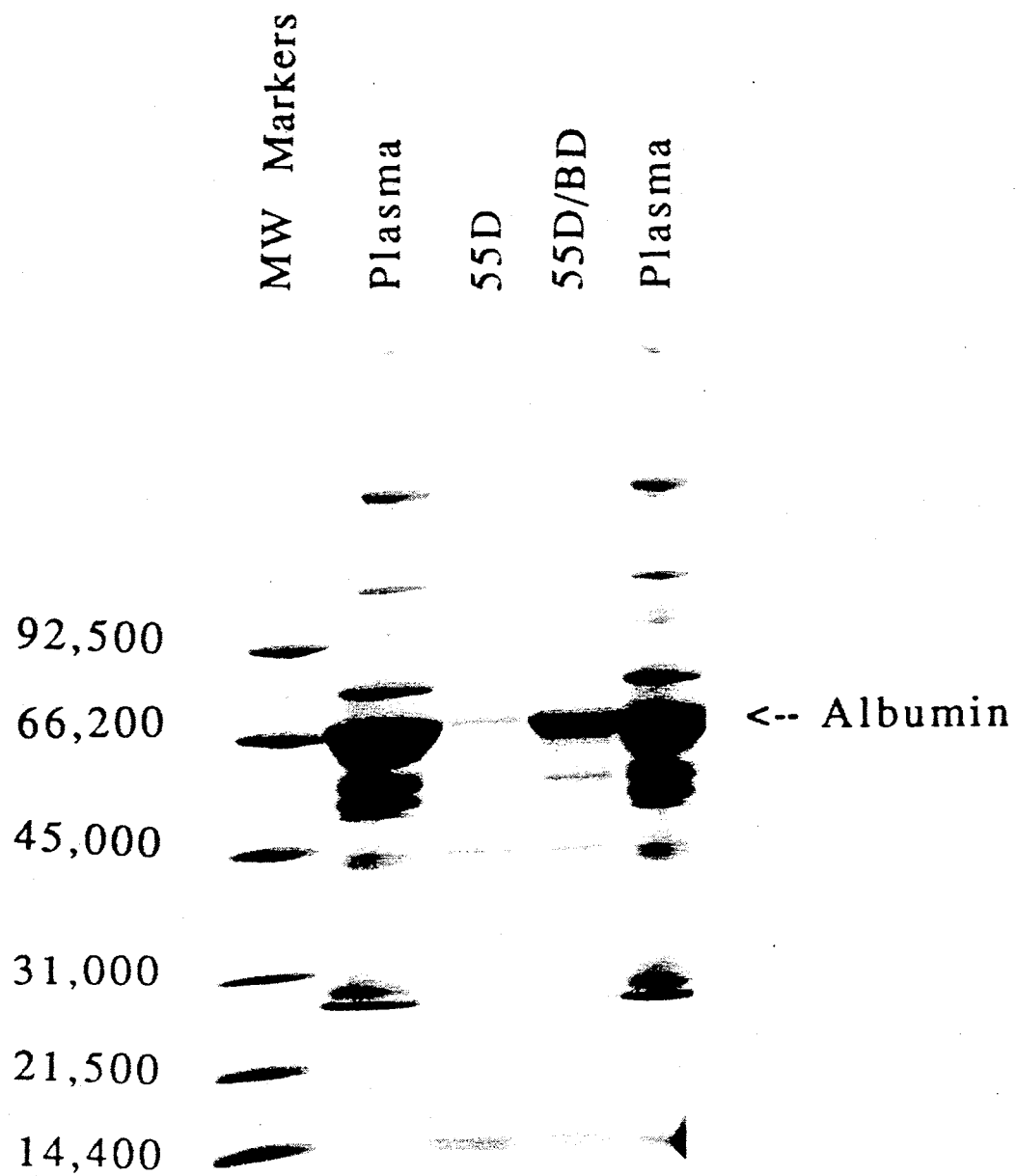
FIG. 3 depicts an SDS-polyacrylamide gel electrophoretogram of proteins eluted from catheters prepared from polyurethane derivatized according to the present method and from non-derivatized polyurethane. The catheters had been previously implanted 24 hours in a mongrel dog.

FIG. 3 depicts the SDS-polyacrylamide gel electrophoretogram of proteins eluted from the catheters. As shown in FIG. 3, the results of this experiment indicate that a large number of plasma proteins remained adherent to the polyurethane catheter material. However, the polyurethane derivatized with Blue Dextran had very few visible protein bands, the predominant one being canine albumin, which is slightly smaller than the human protein shown in FIG. 1. Note the large number and high concentration of proteins present on the surface of the non-derivatized polyurethane catheter (lane 2) compared with the small number of proteins present on the surface of the Blue Dextran-derivatized material (lane 3). The outer two lanes contain the same molecular weight standards shown on the gel in FIG. 1.

I. Interactions with Pathogenic Bacteria

The tendency of pathogenic bacteria to adhere to various non-derivatized polymeric materials and to derivatized Pellethane TM 55D polyurethane prepared according to Part A above was estimated by measuring the numbers of adherent *Staphylococcus epidermidis*, the most frequent cause of infections associated with implanted devices. *S. epidermidis*, isolated from a patient with an infected catheter, were grown overnight in Brain Heart Infusion (Gibco, Inc., Grand Island, N.Y.). The bacteria were concentrated centrifugally and washed three times in phosphate buffered saline.

Following washing, the bacteria were resuspended to a concentration of $7 \times 10^6$/ml, and small pieces of each of the polymers listed in Table 4 below, affixed to glass slides, were immersed in the bacteria suspension with gentle mixing for 30 mins at 25° C. The slides were then washed with four changes of 1,000 volumes of phosphate buffered saline, dried, fixed in methanol, and stained with Giemsa Stain (Sigma Chemical Co., St. Louis, MI.).

Table 4 below lists the number of adherent bacteria per square mm of each of the various polymeric materials tested. None of the polymeric materials included in Table 4 was derivatized except for Pellethane TM 55D, as noted. The results listed in Table 4 indicate that whereas large numbers of bacteria adhered to the non-derivatized polyurethane, very few Staphylococci remained associated with the Blue Dextran-derivatized polyurethane.

TABLE 4

Adherence of *Staphylococcus epidermis* (Clinical Isolate) to Control and Blue Dextran-Derivatized Polyurethane and Other Polymers

| Material | Bacteria per mm$^2$ |
| --- | --- |
| Pellethane TM 55D (Upjohn) derivatized with Blue Dextran | 0* |
| Pellethane TM 55D (Upjohn) | 5300 |
| Pellethane TM 75D (Upjohn) | 2200 |
| Pellethane TM 80A (Upjohn) | 6700 |
| Pellethane TM 80AE (Upjohn) | 1500 |
| Biomer TM (Ethicon) | 2100 |
| Estane TM 5701 (B. F. Goodrich) | 4000 |
| Estane TM 5714 (B. F. Goodrich) | 3100 |
| Lexan TM polycarbonate (General Electric) | 1500 |
| Marlex TM polyethylene HD (Phillips) | 1400 |
| Marlex TM polypropylene (Phillips) | 2600 |
| Tecoflex TM (Thermedics) | 1700 |

TABLE 4-continued

Adherence of *Staphylococcus epidermis* (Clinical Isolate) to Control and Blue Dextran-Derivatized Polyurethane and Other Polymers

| Material | Bacteria per mm$^2$ |
| --- | --- |
| Teflon TM (DuPont) | 900 |

*Differs from samples of non-derivatized Pellethane TM 55D, p < 0.0001 (Student's 't' test, two-tailed)

In the above experiments, additional comparisons were made with other non-derivatized plastics. Most of these also accumulated relatively large numbers of bacteria.

EXAMPLE II

Derivatization of Other Polymers

Blue Dextran was also incorporated into Silastic TM MDX-4-4210 silicone elastomer (Dow Corning, Midland, MI.) and Lexan TM polycarbonate (General Electric, Pittsfield, MA.). Blue Dextran was incorporated into the Silastic as follows: 1.2 g Blue Dextran was mixed with 2.0 g water This mixture was then added to 4.3 g of Silastic TM MDX-4-4210 prior to curing. Incorporation of the Blue Dextran into polycarbonate was accomplished by dissolving 0.44 g Blue Dextran in 1.58 g water and 34.65 g DMAC. 0.68 g Lexan TM was then dissolved in this solvent system, cast on a Mylar release sheet, and dried overnight at 50° C.

EXAMPLE III

Derivitization with Free Dye

Free (i.e., non-conjugated) Reactive Blue 2 dye (also commercially available as Cibacron Blue) was incorporated into Pellethane TM 55D (Upjohn) using the same technique as previously described in Example I for Blue Dextran incorporation into Pellethane TM 55D. The following amounts were used: 1.0 g dye, 1.10 g Pellethane TM 55D, 1.5 g water and 27 g DMAC (Fisher Scientific, Pittsburgh, PA.)

Reactive Blue 2 dye was also chemically bonded to the surface of a Biomer198 film (Ethicon). The film was plasma treated with ammonium-generating reactive amine groups in order to place the amine groups on the surface of the film, and the dye was then chemically bonded to these reactive groups.

Reactive Blue 2 dye was also attached to the surfaces of Biomer=(Ethicon, Sommerville, N.J.), EstaneTM 5701 (B. F. Goodrich, Cleveland, OH.), and Silastic TM (Dow Corning, Midland, MI.) using tridodecylammonium chloride (TDMAC) as a coupling agent. In the case of Biomer TM and EstaneTM 5701, the dye and TDMAC were added to ethanol, and the dye-TDMAC complex was then swelled into the surfaces of the Biomer TM and Estane TM 5701. In the case of silicone, the Reactive Blue 2 dye and TDMAC were added to xylene, and the dye-TDMAC complex was then swelled into the silicone surface.

It is expected that the materials formed by the procedures of Examples II and III will also be effective to bind albumin when contacted with physiological or synthetically prepared fluids containing albumin.

The invention has been described with reference to various specific and preferred embodiments and techniques. However, it should be understood that many variations may be made while remaining within the spirit and scope of the invention.

What is claimed is:

1. A biocompatible prosthetic device having a solid polymeric body incorporating an amount of an albumin-binding dye effective to provide a means to form a coating of endogenous albumin on said device when said device is in contact with a physiological fluid containing albumin.

2. The biocompatible prosthetic device of claim 1 wherein said albumin-binding dye comprises an aromatic albumin-binding dye.

3. The biocompatible prosthetic device of claim 2 wherein said aromatic albumin-binding dye comprises a diazo dye; a sulfonic acid dye; or the physiologically-acceptable salts thereof.

4. The biocompatible prosthetic device of claim 3 wherein said aromatic albumin-binding dye is selected from the group consisting of Reactive Blue 2, Evans Blue, Trypan Blue, Bromcresol Green, Bromcresol Purple, Methyl Orange, 2-(4'-hydroxyazobenzene)benzoic acid, Procion red HE 3B, and mixtures thereof.

5. The biocompatible prosthetic device of claim 1 wherein said albumin-binding dye is conjugated to a physiologically acceptable water-soluble polysaccharide.

6. The biocompatible prosthetic device of claim 5 wherein said polysaccharide comprises dextran.

7. The biocompatible prosthetic device of claim 6 wherein said albumin-binding dye comprises an aromatic albumin-binding dye.

8. The biocompatible prosthetic device of claim 7 wherein said aromatic albumin-binding dye comprises a diazo dye; a physiologically acceptable salt of said diazo dye; a sulfonic acid dye; a physiologically acceptable salt of said sulfonic acid dye; or mixtures thereof.

9. The biocompatible prosthetic device of claim 8 wherein said aromatic albumin-binding dye is selected from the group consisting of Reactive Blue 2, Evans Blue, Trypan Blue, Bromcresol Green, Bromcresol Purple, Methyl Orange, 2-(4'-hydroxyazobenzene)benzoic acid, Procion red HE 3B, and mixtures thereof.

10. The biocompatible prosthetic device of claim 1 wherein said solid polymeric body comprises a polyurethane, a silicone elastomer, a polycarbonate, or mixtures thereof.

11. The biocompatible prosthetic device of claim 10 wherein said polyurethane comprises a polyether polyurethane.

12. The biocompatible prosthetic device of claim 10 wherein said silicone elastomer comprises a medical grade elastomer.

13. The biocompatible prosthetic device of claim 1 wherein the endogenous albumin is human serum albumin.

14. The biocompatible prosthetic device of claim 1 wherein said device is a catheter.

15. The biocompatible prosthetic device of claim 1 wherein said device is a heart valve.

16. The biocompatible prosthetic device of claim 1 wherein said device is a vascular graft.

17. The biocompatible prosthetic device of claim 1 wherein the physiological fluid is blood, lymph, saliva, urine, tears or cerebro-spinal fluid.

18. A method of increasing the albumin-binding ability of a prosthetic device having a solid polymeric body, said method comprising the step of:
   (a) incorporating into said polymeric body an amount of an albumin-binding dye; wherein the amount of the albumin binding dye is effective to provide a means to form a coating of endogenous albumin on a surface of said polymeric body when the surface is in contact with a physiological fluid containing albumin.

19. The method of claim 18 wherein the albumin-binding dye comprises an aromatic albumin-binding dye.

20. The method of claim 19 wherein the aromatic albumin-binding dye comprises a diazo dye; a physiologically acceptable salt of said diazo dye; a sulfonic acid dye; a physiologically acceptable salt of said sulfonic acid dye; or mixtures thereof.

21. The method of claim 20 wherein the aromatic albumin-binding dye is selected from the group consisting of Reactive Blue 2, Evans Blue, Trypan Blue, Bromcresol Green, Bromcresol Purple, Methyl Orange, 2-(4-hydroxyazobenzene)benzoic acid, Procion red HE 3B, and mixtures thereof.

22. The method of claim 18 wherein the physiological fluid is blood, lymph, saliva, urine, tears, or cerebrospinal fluid.

* * * * *